(12) United States Patent
Rahme et al.

(10) Patent No.: US 11,972,847 B2
(45) Date of Patent: Apr. 30, 2024

(54) METHOD AND SYSTEM FOR ASYNCHRONOUS MEDICAL PATIENT DATA COMMUNICATION AND MANAGEMENT

(71) Applicant: Authentic, Inc., Bingham Farms, MI (US)

(72) Inventors: Kamil Rahme, Scottsdale, AZ (US); Alan Best, Big Bend, WI (US); Jeffrey Santoso, Dural (AU); Josh Howerter, Phoenix, AZ (US)

(73) Assignee: Authentic, Inc., Bingham Farms, MI (US)

( * ) Notice: Subject to any disclaimer, the term of this patent is extended or adjusted under 35 U.S.C. 154(b) by 0 days.

(21) Appl. No.: 18/073,979

(22) Filed: Dec. 2, 2022

(65) Prior Publication Data

US 2023/0155985 A1   May 18, 2023

Related U.S. Application Data

(63) Continuation of application No. 17/942,054, filed on Sep. 9, 2022.

(60) Provisional application No. 63/278,960, filed on Nov. 12, 2021.

(51) Int. Cl.
| | |
|---|---|
| *G16H 10/60* | (2018.01) |
| *G06F 21/62* | (2013.01) |
| *H04L 9/40* | (2022.01) |
| *H04L 67/12* | (2022.01) |

(52) U.S. Cl.
CPC ......... *G16H 10/60* (2018.01); *G06F 21/6245* (2013.01); *H04L 63/0428* (2013.01); *H04L 63/10* (2013.01); *H04L 67/12* (2013.01)

(58) Field of Classification Search
CPC ..... H04L 63/0428; H04L 63/10; H04L 67/12; G06F 21/6245; G16H 10/60
See application file for complete search history.

(56) References Cited

U.S. PATENT DOCUMENTS

| | | | |
|---|---|---|---|
| 6,587,867 B1 * | 7/2003 | Miller | H04Q 3/0033 709/200 |
| 7,685,417 B2 * | 3/2010 | Wise | H04N 1/00209 718/1 |

(Continued)

OTHER PUBLICATIONS

International Search Report and Written Opinion of the International Search Authority for International Application No. PCT/US22/43152 dated Jan. 3, 2023, 6 pages.

(Continued)

*Primary Examiner* — Michael R Vaughan
(74) *Attorney, Agent, or Firm* — DICKINSON WRIGHT PLLC

(57) ABSTRACT

An asynchronous system for managing medical file protection and distribution. The system controls the distribution of sensitive patient records between different healthcare entities. The system includes a registration process for the healthcare institutions which creates a secure gateway between the system and the healthcare institution. Once registered, the system creates a content queue on the server for content designated to be sent to the institution. The client device of the healthcare institution will poll the queue and download the medical file content as it becomes available.

20 Claims, 6 Drawing Sheets

(56) References Cited

U.S. PATENT DOCUMENTS

| | | | |
|---|---|---|---|
| 8,706,877 B2* | 4/2014 | Sundarrajan | H04L 67/34 |
| | | | 709/227 |
| 10,790,056 B1* | 9/2020 | Accomazzi | H04L 67/1095 |
| 10,848,534 B2* | 11/2020 | Namboodiri | H04L 65/612 |
| 11,582,065 B2* | 2/2023 | Burd | G06Q 50/26 |
| 2002/0019751 A1* | 2/2002 | Rothschild | H04N 1/00209 |
| | | | 705/3 |
| 2003/0046587 A1 | 3/2003 | Bheemarasetti et al. | |
| 2011/0145693 A1 | 6/2011 | Mutic et al. | |
| 2016/0210408 A1 | 7/2016 | Yu et al. | |
| 2016/0314458 A1* | 10/2016 | Douglas | G06Q 20/3674 |
| 2020/0137097 A1 | 4/2020 | Zimmermann et al. | |
| 2020/0161003 A1 | 5/2020 | Wright et al. | |
| 2021/0057064 A1 | 2/2021 | LaBorde et al. | |
| 2021/0151147 A1 | 5/2021 | Dempers et al. | |
| 2021/0158931 A1* | 5/2021 | Tweedie | H04L 67/12 |
| 2022/0214916 A1* | 7/2022 | Mundra | G06F 9/4887 |

OTHER PUBLICATIONS

International Search Report from PCT/US23/29393 dated Dec. 8, 2023.

\* cited by examiner

METHOD AND SYSTEM FOR ASYNCHRONOUS MEDICAL PATIENT DATA COMMUNICATION AND MANAGEMENT

CROSS-REFERENCES TO RELATED APPLICATION

This Continuation Patent Application claims priority to and the benefit to U.S. patent application Ser. No. 17/942,054 filed Sep. 9, 2022, which claims priority to and the benefit of U.S. Provisional Patent Application Ser. No. 63/278,960, filed Nov. 12, 2021, the entire disclosures of which are hereby incorporated by reference.

FIELD OF THE DISCLOSURE

The present disclosure relates to an asynchronous medical patient data communication and management system. More particularly, the system of the present disclosure facilitates the secure communication of patient document files between healthcare providers with distinct internal IT networks.

BACKGROUND OF THE DISCLOSURE

This section provides background information related to the present disclosure which is not necessarily prior art.

Hospital systems must manage large troves of sensitive user data. Such data has unique security regulations that lead to cumbersome security protocols. The data typically must be accessible by various individuals within a particular health care institution's internal network, such as doctors and staff. The data often must also be shareable with other parties, such as medical laboratories, clinics, and other health care systems. The increased security protocols, huge amount of data, and large number of people that must access the data leads to unique challenges faced by large healthcare institutions.

Often health care providers are required to share patient data in order to serve the patient. For example, scans of the patient (e.g., X-ray, MRI, CAT) are commonly analyzed by radiologists working off-site for a different healthcare entity. Without a secure means for transferring the data quickly, healthcare outcomes may suffer.

Hospitals are correctly cautious in granting full access to their internal database to external healthcare entities. Often access is limited to protect the privacy of patient information stored by the hospital. In order to grant access, hospitals often require paperwork to be filed, and associated review and granting of permission by hospital personnel.

Another concern that requires high data security is a need to comply with all current and future health care IT laws (such as HIPAA). HIPAA requires that hospitals limit access to their IT to authorized employees only. Sharing of health data between health care entities requires authentication between the systems. Violation of HIPAA policies can lead to considerable civil penalties.

Hospitals have attempted to utilize physical storage as a means of data exchange. Such means include a CD-ROM or portable memory device. In this instance, relevant data is loaded on the device and delivered to another health care entity. Such a transfer avoids granting remote access to patient data at all. However, this approach is very time consuming and dependent on mail services. The increasing size of data files is another concern, as physical media is generally not intended to transfer the scale of data required for high resolution 3D images.

In order to set up a secure connection between to health care providers, the process often depends on proprietary hardware being transferred from one provider to the other. If hardware is not required, then personnel from one entity must install and authenticate the necessary permission on the client device of the opposing health care entity. Both such approaches are typically time and resource intensive in order to create the network connection.

In view of the foregoing, a method is desired that allows a health care entity to create a secure authenticated connection with another entity for the purpose of transferring patient files that only needs downloading and installing of software at the client device.

SUMMARY OF THE DISCLOSURE

This section provides a general summary of the disclosure and is not intended to be interpreted as a comprehensive listing of its full scope or of all of its objects, aspects, features and/or advantages.

It is an aspect of the disclosure to provide a patient data storage and transfer system which is remotely installed and authenticated. A software instruction package is obtained by a network connection and used to create an authenticated secure connection between the client device of the health care entity and the remote computing device hosting the system. The system further generates a unique ID value based on at least one property of the client device. The system uses the ID value in order to create a unique client-side queue and a server-side queue. The server-side queue being polled by the client device, causing the client device to perform the commands stored therein. The client-side queue being polled by the remote computing device, causing the remote computing device to execute the commands stored therein.

It is another aspect of the disclosure to provide a system for securely sharing patient data that includes, in one implementation, data encryption of medical images files. The system is configured to limit access to only authorized parties. The authenticated connection creates a secure bidirectional gateway between the client device and the remote computing device.

Other technical features may be readily apparent to one skilled in the art from the following figures, descriptions, and claims.

DRAWINGS

The drawings described herein are for illustrative purposes only of selected embodiments and not all possible implementations thereof such that the drawings are not intended to limit the scope of the present disclosure.

Figure 5:
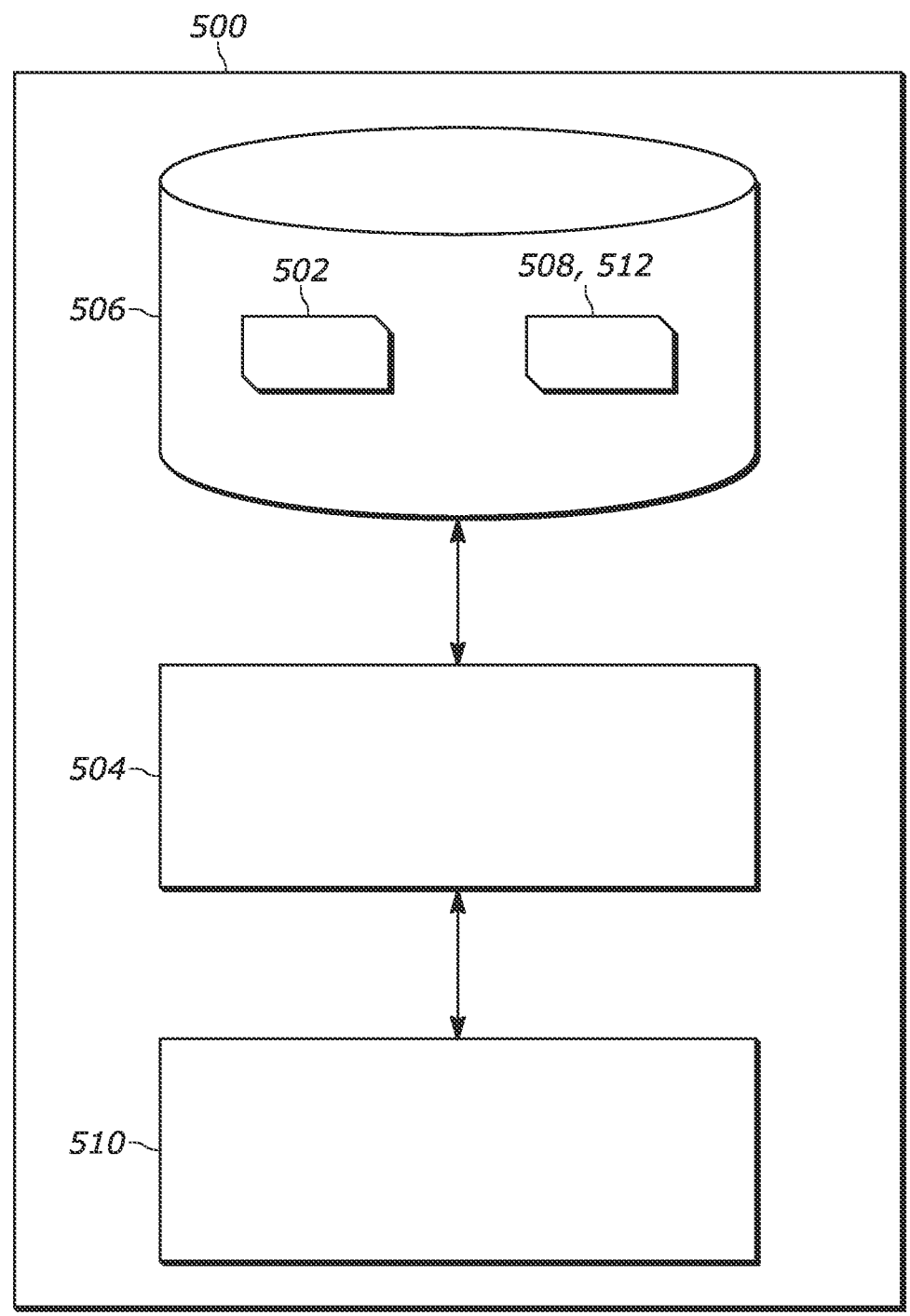

FIG. 5 generally illustrates a system for training a neural network, according to the principles of the present disclosure.

Figure 6:
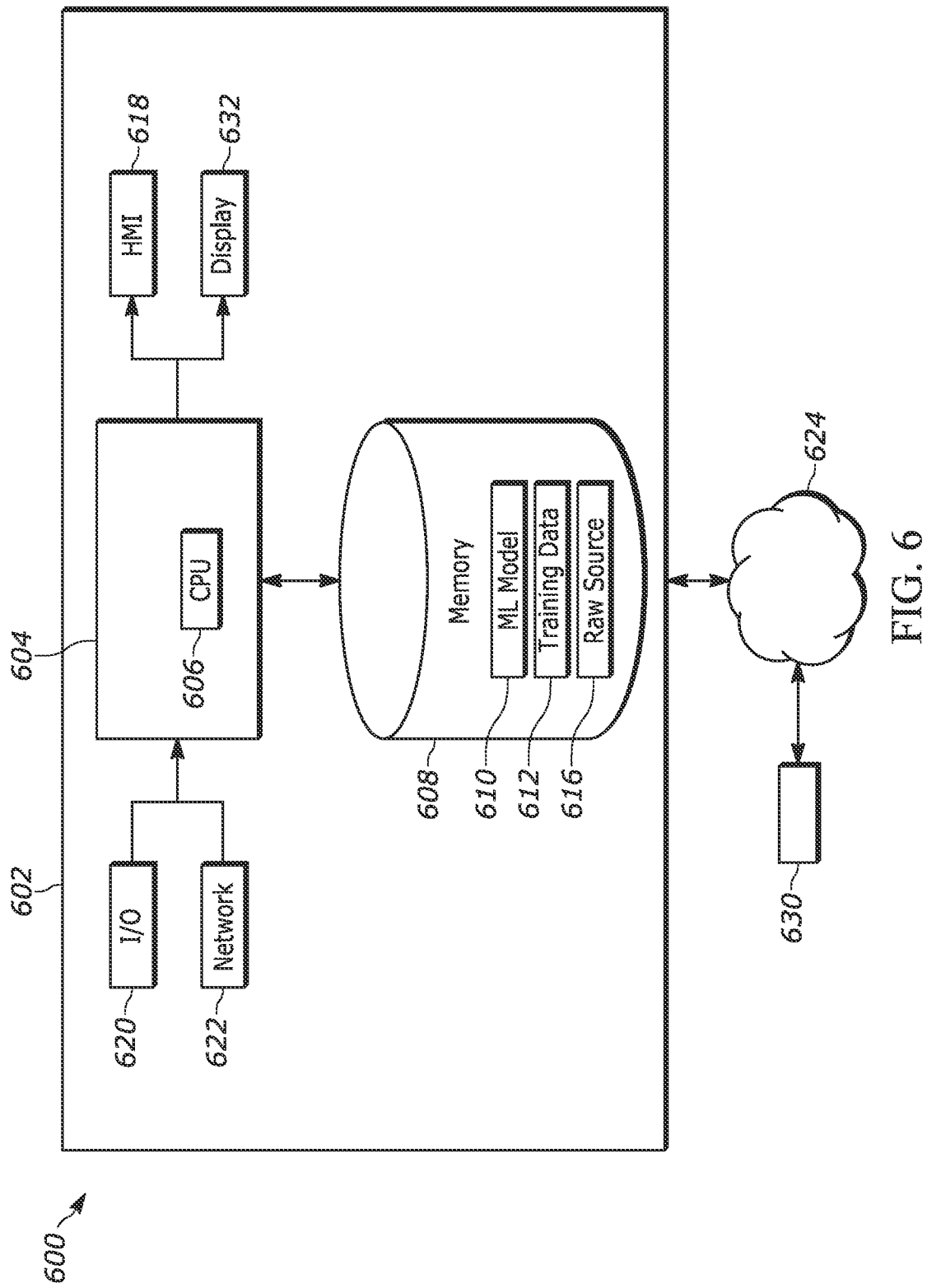

FIG. 6 generally illustrates a computer-implemented method for training and utilizing a neural network, according to the principles of the present disclosure.

Corresponding reference numerals indicate corresponding parts throughout the several view of the drawings.

DETAILED DESCRIPTION OF THE EXAMPLE EMBODIMENT

Example embodiments of a patient document management system embodying the teachings of the present disclosure will now be described more fully with reference to the accompanying drawings. However, the example embodiments are only provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that the example embodiments may be embodied in many different forms that may be combined in various ways, and that neither should be construed to limit the scope of the disclosure. In some example embodiments, well-known processes, well-known device structures, and well-known technologies are not described in detail.

Figure 1:
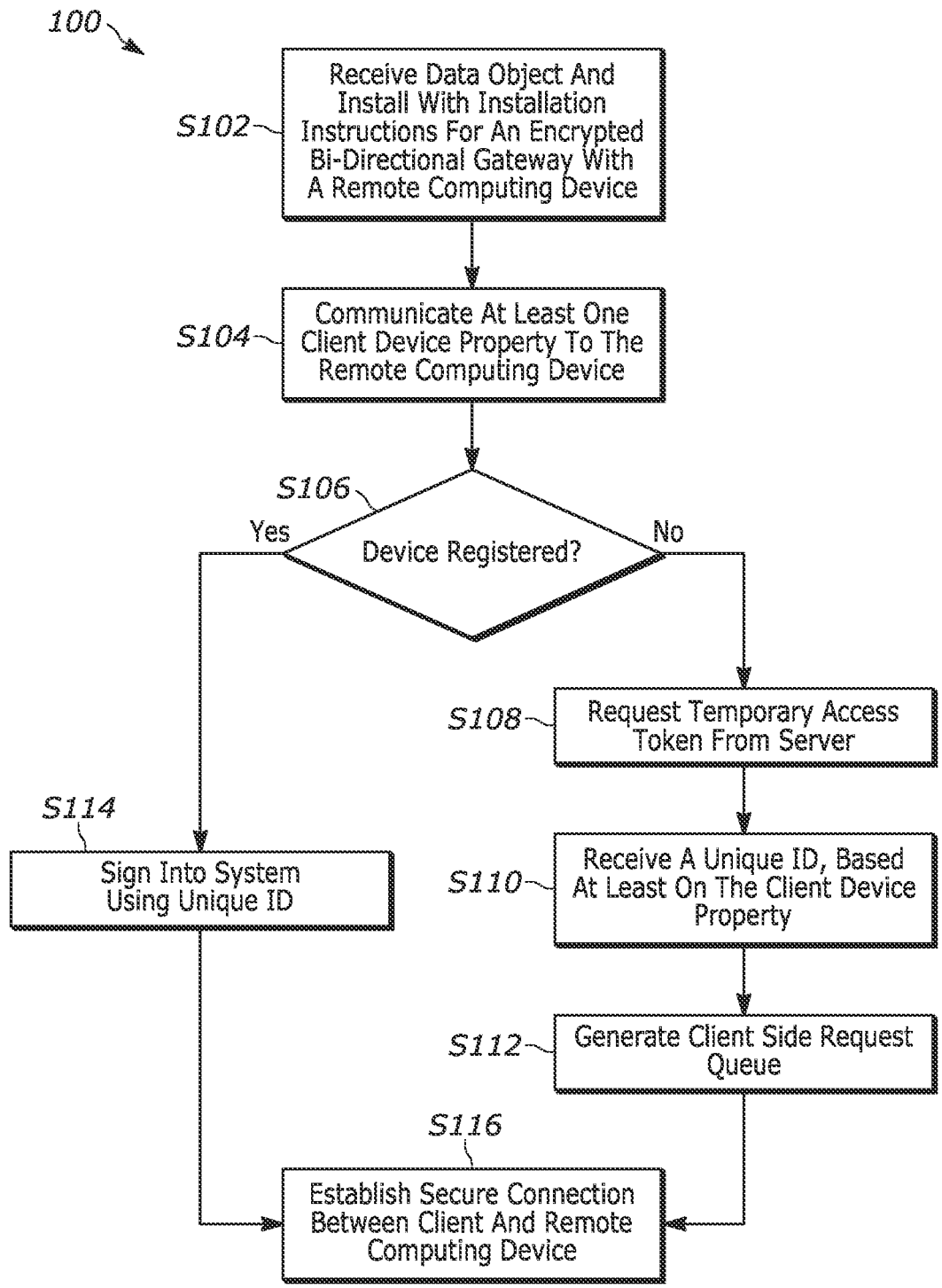
FIG. 1 is a block diagram of an example of a system for patient data management, in accordance with some implementations of the present disclosure.

FIG. 1 is a block diagram of an example of a method 100 for authenticating a device and establishing a secure connection with the remote computing device. The method 100 illustrated in FIG. 1 begins with the client device receiving a data object S102. The client device executes the instructions found in the data object which is configured to install system component on the client device. The process than moves on to S104, where the client device makes an unauthorized connection with the remote computing device. Using the unauthorized connection, the client device communicates at least one device property to the remote computing device. The remote computing device uses the received device property in order to determine if the device is already registered to the system.

If the device is not registered, the method moves on to S108, where the client device requests a temporary authentication token from the remote computing device. If the client has already attempted multiple registrations, the remote computing device refuses to provide the token. Otherwise, the remote computing device will provide an authentication token that is valid for a predetermined amount of time (e.g., 1 hour). The method then continues to S110, where the remote computing device generates a unique ID value for the client device based at least in part on the client device property received in S104. Now that the client device is fully authenticated, the system generates a client-side queue for collecting commands input by the user.

In a scenario where the system finds that the client device has been previously registered in S106, the method then moves on to S114. The system uses the unique ID value associated with the client device to fully authenticate the connection to the remote computing device in S116. The secure connection created is bidirectional and allows the transfer of secure patient data between computers over a network. Content is encrypted before it is sent and decrypted once it is received. In an additional scenario, at S106 an unregistered device that has already made multiple attempts to become authenticated will be denied further access to the system.

Figure 2:
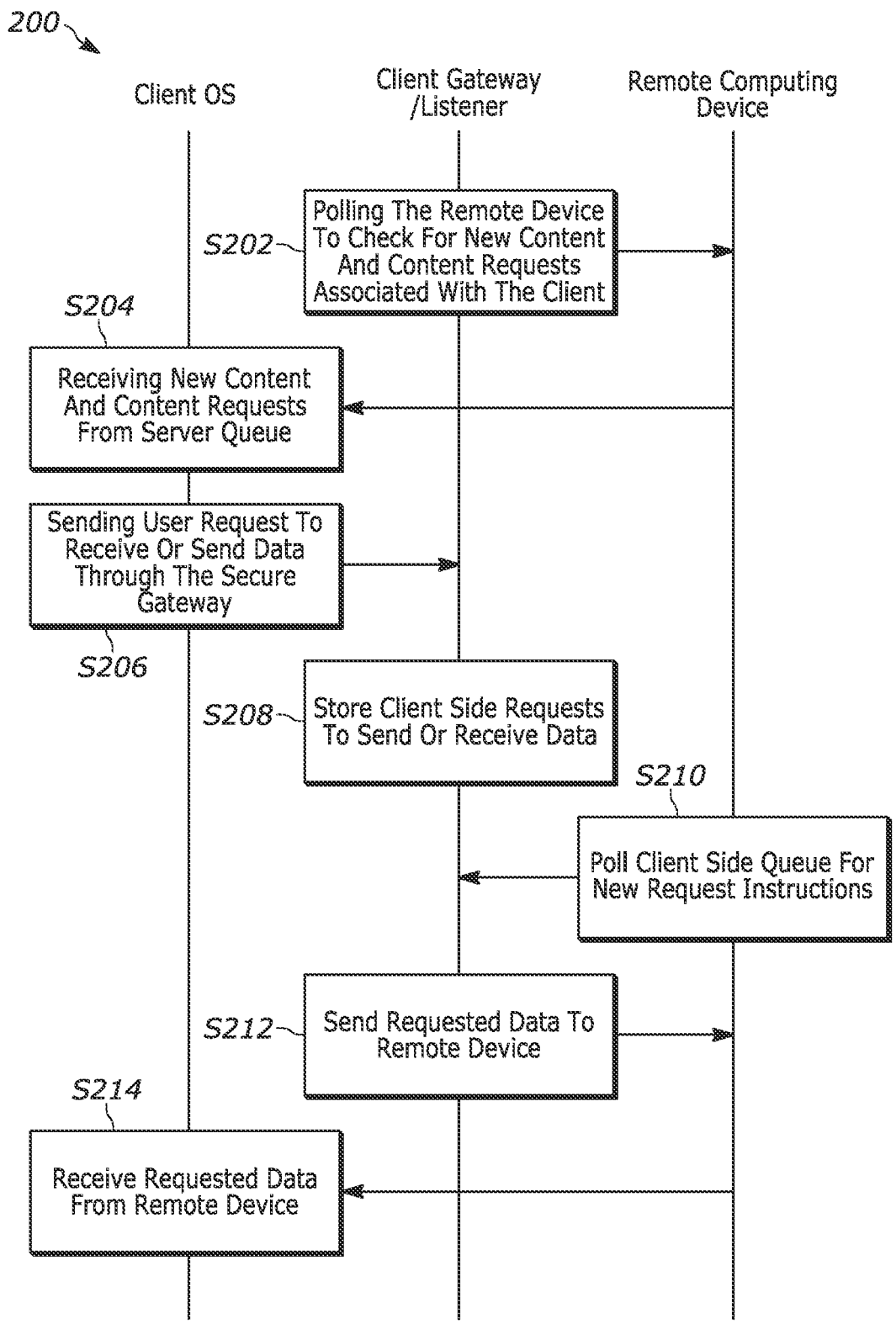
FIG. 2 is a block diagram of an example process for operating the system described in FIG. 1, in accordance with some implementations of the present disclosure.

FIG. 2 is a block diagram illustrating how the components of the system interact with one another over a network after a secure connection has been established. At S202, the client-side gateway application polls the server-side unique queue for new commands. The client receives the commands stored in the queue since the last polling request. Commands may include a command to find a specific patient file (e.g., C-Find), a command to transfer a file (e.g., C-Move), or document previously requested for receipt by the client device.

At S204, the client device receives the previously requested documents and commands that were stored in the server-side unique queue. The client regularly polls the serve-side unique queue for updates and automatically receives waiting files and executes waiting commands. At S206, a user interacting with the client device inputs a command requesting to find or move a document from the system, or otherwise interact with the system. At S208, the client device passes the commands to the client-side application which stores it in the client-side unique queue.

At S210, the remote computing device polls the client-side unique queue and receives any new commands entered by users on the client device. At S212, the client computing device sends and receives the patient documents based on the commands stored in the unique client-side queue. Finally, at S214, the client computing device receives the documents requested by the commands stored in the unique client-side queue.

Figure 3:
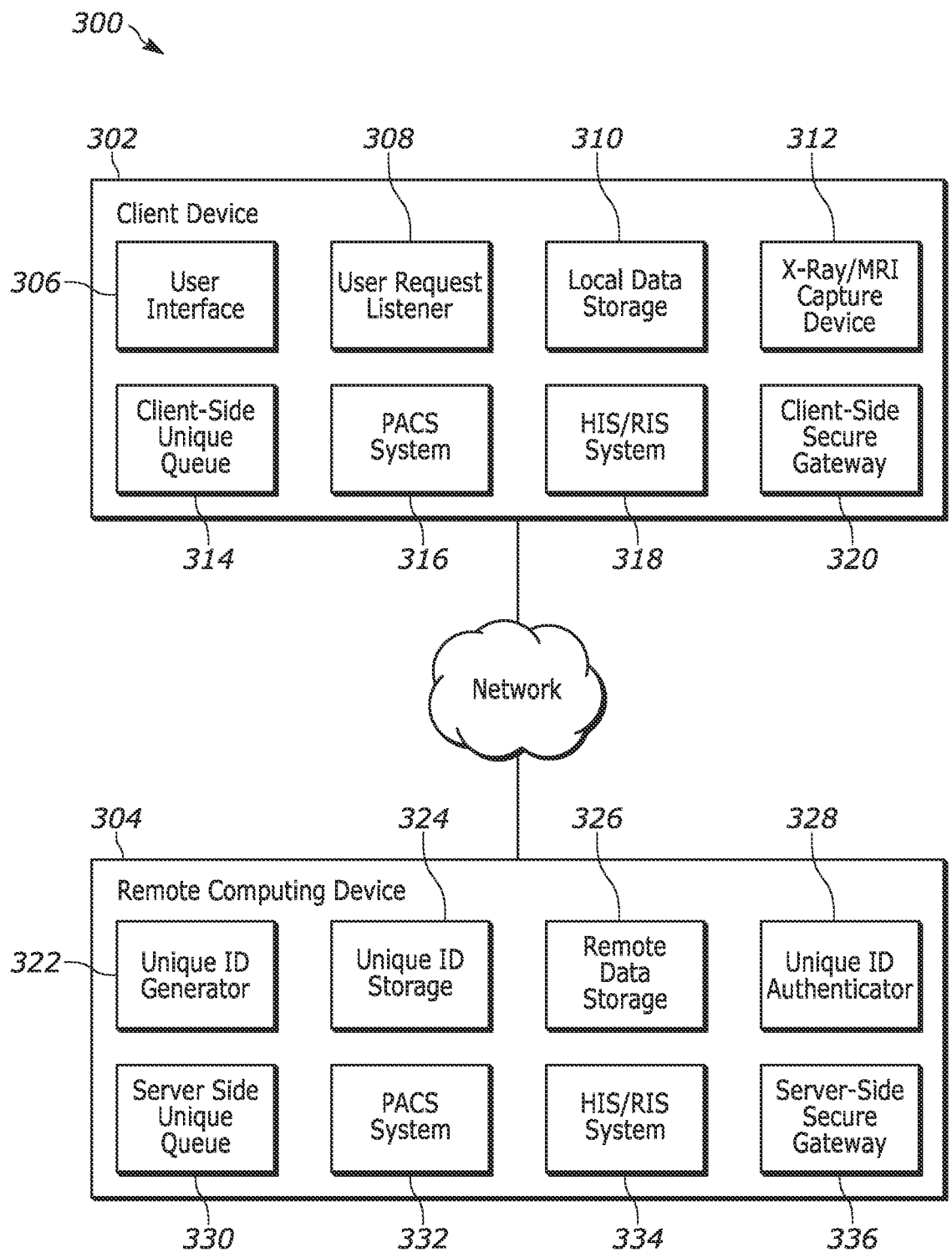
FIG. 3 is a block diagram of an example of system devices and their components, in accordance with some implementations of the present disclosure.

FIG. 3 is a component view of the invention, specifically of the client device 302 and the remote computing device 304. The client device is a computer having at least a processor and running an operating system (e.g., MS WINDOWS, APPLE OSX, CHROME OS, ANDROID, LINUX, APPLE iOS). The client device 302 includes user interface 306 which allows a user to input commands. The user interface 306 is based on mouse and keyboard inputs, touch based inputs, or any other applicable user interface input method. The user interface 306 allows the user to interact with documents stored on the system and allows the user to make requests for documents they wish to view. When a user inputs a command, the user request listener 308 will recognize the command is intended for the system and stores the command in the client-side unique queue 314.

The client-side unique queue 314 will continue to store new command inputs from the user, a hospital utilizing a PACS system 316 to transfer DICOM images and store commands such as C-Move, and C-Find. A PACS system 316 (picture archiving and communication system) is a medical imaging platform which provides storage and access to patient documents from multiple client devices. Patient files stored by PACS are stored in a format called DICOM (digital imaging and communications in medicine). The overarching administrative tool used to manage that facilitates the intercommunication of these services is the HIS/RIS 318, (hospital information system/radiology information system).

The DICOM images are generated by a scanning modality such as an x-ray and MRI capture device 312. The patient is scanned by capture device 312 and a digital image is created in a DICOM format. The PACS system 316 stores the image in the local data storage 310 of the healthcare entity. The local data storage 310 is a non-transitory computer readable medium. When the user inputs a command to send an image from the local data storage 310 to another health care entity, that command will be stored by the client-side unique queue 314 until the queue is polled by the remote computing device 304.

When the remote computing device 304 polls the client-side unique queue 314, any commands for receiving or sending DICOM images via the PACS system 316 will be authenticated by the client-side secure gateway 320. The client-side secure gateway 320 encrypts messages before they depart and decrypts them when they arrive from the remote computing device 304.

The remote computing device 304 includes components to mirror that of the client computing device 302, such as the server-side secure gateway 336, PACS system 332, and HIS/RIS system 334. The server-side secure gateway 336 mirrors the functionality of the client-side secure gateway 320. Patient documents will be decrypted on arrival and encrypted before departure. Once received those documents are stored in the remote data storage 326 which is a non-transitory computer readable medium.

Unique to the remote computing device 304 are components associated with registration and authentication of the client computing device 302. The components include the unique ID generator 322, unique ID storage 324, and the unique ID authenticator 328. The unique ID generator 322 creates the unique ID values based on at least one component of the client computing device 302. Many components are used such as an Item Unique Identification (IUID) number, Unique Identification (UID) number or other components unique to the device 302. Unique ID storage 324 stores all the unique ID values generated by the unique ID generator 322. All devices registered to the system from all the healthcare entities subscribed to the system will have a matching unique ID stored in the unique ID storage 324. Finally, the unique ID authenticator 328 controls the process of requesting the unique ID from a registered client device and comparing it against the unique IDs stored in the unique ID storage 324. Based on that analysis, the unique ID authenticator will determine if the device being authenticated is registered. Based on that determination, the system will either allow access of begin a registration process.

Remote computing device 304 provides the cloud support for the system. All healthcare entities subscribed to the system will have their own client device 302 that facilitates communication with the remote computing device 304. Different healthcare entities communication with one another is facilitated by the remote computing device 304.

Figure 4:
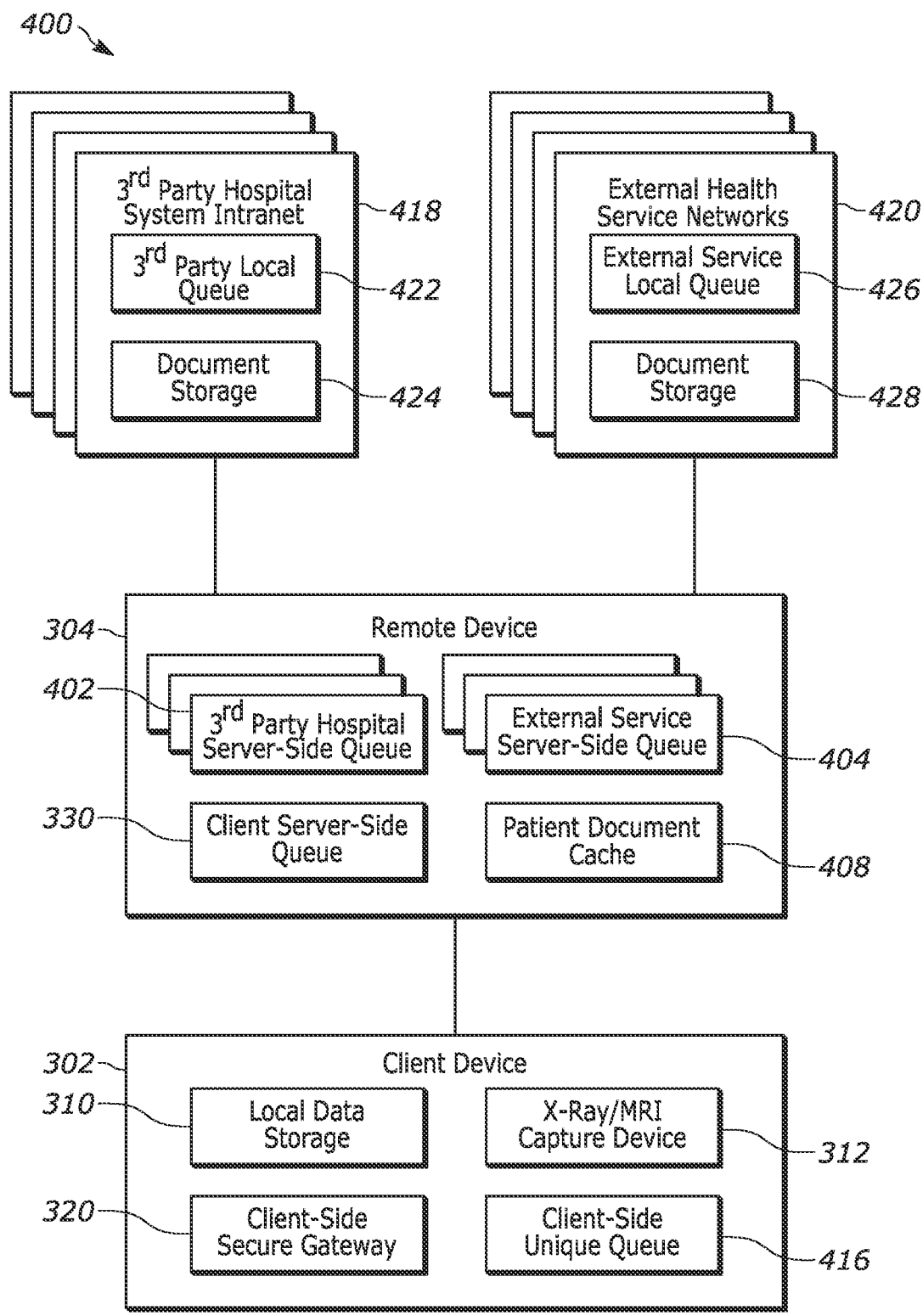
FIG. 4 is a block diagram of an example network of subscriber devices interacting with the client device, facilitated by a remote computing device of the system, in accordance with some implementation of the present disclosure.

FIG. 4 is a diagram illustrating how the system operates, not simply between the client and the remote system server 304 as in FIG. 3, with a network of subscribers all authenticated and communicatively coupled to the remote computing device 304. The remote device 304 facilitating all communication between subscribers of the system. From the perspective of a healthcare entity (e.g., hospital, medical clinic, etc.) access to the system is facilitated by a client device 302 which is already been authenticated and connected to the remote device 304. The healthcare entity will require transfer of documents to and from at least two groups, $3^{rd}$ Party healthcare systems 418 (e.g., hospitals medical clinics, hospital systems), and healthcare services 420 (i.e., medical labs, radiologist contractors, Doctors providing second opinions, insurance companies) with their own internal network.

The client-side queue 416 is unique to the healthcare entity using it. When the healthcare entity uses the client device to request or send a patient document, the command is stored in the client-side queue 416 until the client communicates them to the remote device 304. The commands are stored in the client server-side queue 330 that is associated with the client 302. Patient documents related to send requests are stored in the patient document cache 408. Requests to retrieve documents from a $3^{rd}$ party hospital system will be stored in the $3^{rd}$ party hospital server-side queue 402. Requests to retrieve documents from external health services will also be stored in the external service server-side queue 404. The documents related to the request is received by the remote computing device 304 and stored in the patient document cache 408.

The $3^{rd}$ party hospital system intranet 418 communicates with the remote device 304 and polls its unique $3^{rd}$ party hospital server-side queue. Any send or receive commands in the 3rd party hospital server-side queue will be sent to the $3^{rd}$ party hospital system intranet 418 and executed by their system. Requested documents that were sent by another subscriber will be downloaded from the patient document cache 408. Requested documents will be uploaded and stored in the patient document cache with its associated command stored in the unique queue of the recipient. External health network 420 largely operates in the same manner as other subscribers but can be restricted in what they send or receive. Further, the documents sent to the external health service network 420 can be set to automatically delete after a predetermined time period.

FIG. 5 shows a system 500 for training a neural network. The system 500 may comprise an input interface for accessing training data 502 for the neural network. For example, as illustrated in FIG. 5, the input interface may be constituted by a data storage interface 504 which may access the training data 502 from a data storage 506. For example, the data storage interface 504 may be a memory interface or a persistent storage interface, e.g., a hard disk or an SSD interface, but also a personal, local or wide area network interface such as a Bluetooth, Zigbee or Wi-Fi interface or an ethernet or fiberoptic interface. The data storage 506 may be an internal data storage of the system 500, such as a hard drive or SSD, but also an external data storage, e.g., a network-accessible data storage.

In some embodiments, the data storage 506 may further comprise a data representation 108 of an untrained version of the neural network which may be accessed by the system 500 from the data storage 506. It may be appreciated, however, that the training data 502 and the data representation 508 of the untrained neural network may also each be accessed from a different data storage, e.g., via a different subsystem of the data storage interface 504. Each subsystem may be of a type as is described above for the data storage interface 504.

In some embodiments, the data representation 508 of the untrained neural network may be internally generated by the system 500 on the basis of design parameters for the neural network, and therefore may not explicitly be stored on the data storage 506. The system 500 may further comprise a processor subsystem 510 which may be configured to, during operation of the system 500, provide an iterative function as a substitute for a stack of layers of the neural network to be trained. Here, respective layers of the stack of layers being substituted may have mutually shared weights and may receive as input-output of a previous layer, or for a first layer of the stack of layers, an initial activation, and a part of the input of the stack of layers.

The system 500 may further comprise an output interface for outputting a data representation 512 of the trained neural network, this data may also be referred to as trained model data 512. For example, as also illustrated in FIG. 5, the output interface may be constituted by the data storage interface 504, with said interface being in these embodiments an input/output (IO') interface, via which the trained model data 512 may be stored in the data storage 506. For example, the data representation 508 defining the 'untrained' neural network may during or after the training be replaced, at least in part by the data representation 512 of the trained neural network, in that the parameters of the neural network, such as weights, hyperparameters and other types of parameters of neural networks, may be adapted to reflect the training on the training data 502. This is also illustrated in FIG. 5 by the reference numerals 508, 512 referring to the same data record on the data storage 106. In some embodiments, the data representation 512 may be stored separately from the data representation 508 defining the 'untrained' neural network. In some embodiments, the output interface may be separate from the data storage interface 504, but may in general be of a type as described above for the data storage interface 504.

FIG. 6a computing system 602. The computing system 602 may include at least one processor 604 that is operatively connected to a memory unit 608. The processor 604 may include one or more integrated circuits that implement the functionality of a central processing unit (CPU) 606. The CPU 606 may be a commercially available processing unit that implements an instruction stet such as one of the x86, ARM, Power, or MIPS instruction set families.

During operation, the CPU 606 may execute stored program instructions that are retrieved from the memory unit 608. The stored program instructions may include software that controls operation of the CPU 606 to perform the operation described herein. In some embodiments, the processor 604 may be a system on a chip (SoC) that integrates functionality of the CPU 606, the memory unit 608, a network interface, and input/output interfaces into a single integrated device. The computing system 602 may implement an operating system for managing various aspects of the operation.

The memory unit 608 may include volatile memory and non-volatile memory for storing instructions and data. The non-volatile memory may include solid-state memories, such as NAND flash memory, magnetic and optical storage media, or any other suitable data storage device that retains data when the computing system 602 is deactivated or loses electrical power. The volatile memory may include static and dynamic random-access memory (RAM) that stores program instructions and data. For example, the memory unit 608 may store a machine-learning model 610 or algorithm, a training dataset 612 for the machine-learning model 610, raw source dataset 616.

The computing system 602 may include a network interface device 622 that is configured to provide communication with external systems and devices. For example, the network interface device 622 may include a wired and/or wireless Ethernet interface as defined by Institute of Electrical and Electronics Engineers (IEEE) 802.11 family of standards. The network interface device 622 may include a cellular communication interface for communicating with a cellular network (e.g., 3G, 4G, 5G). The network interface device 622 may be further configured to provide a communication interface to an external network 624 or cloud.

The external network 624 may be referred to as the world-wide web or the Internet. The external network 624 may establish a standard communication protocol between computing devices. The external network 624 may allow information and data to be easily exchanged between computing devices and networks. One or more servers 630 may be in communication with the external network 624.

The computing system 602 may include an input/output (I/O) interface 620 that may be configured to provide digital and/or analog inputs and outputs. The I/O interface 620 may include additional serial interfaces for communicating with external devices (e.g., Universal Serial Bus (USB) interface).

The computing system 602 may include a human-machine interface (HMI) device 618 that may include any device that enables the system 600 to receive control input. Examples of input devices may include human interface inputs such as keyboards, mice, touchscreens, voice input devices, and other similar devices. The computing system 602 may include a display device 632. The computing system 602 may include hardware and software for outputting graphics and text information to the display device 632. The display device 632 may include an electronic display screen, projector, printer or other suitable device for displaying information to a user or operator. The computing system 602 may be further configured to allow interaction with remote HMI and remote display devices via the network interface device 622.

The system 600 may be implemented using one or multiple computing systems. While the example depicts a single computing system 602 that implements all of the described features, it is intended that various features and functions may be separated and implemented by multiple computing units in communication with one another. The particular system architecture selected may depend on a variety of factors. In some embodiments, the system 600 may be configured to perform the systems and methods described herein, using the system 500 and/or various classical computing algorithms.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in that particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or later, or intervening element or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to described various elements, components, regions, layers and/or sections, these elements, components, regions, layers and/or sections should not be limited by these terms.

These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for securely sharing patient medical data with a client, the method comprising:
   receiving, at a client computing device, a set of instructions;
   instantiating, using the set of instructions, a client-side gateway configured to provide secure connection between the client computing device and a remote computing device;
   generating, by the remote computing device, a unique identification value for the client computing device based on at least one property of the client computing device;
   storing, by a picture archiving and communication system (PACS) system, medical data having a DICOM format at a local data storage memory of the client computing device;
   generating, by the remote computing device, a server-side queue associated with the unique identification value of the client computing device and containing a command to move the medical data from the local data storage memory to another healthcare entity, wherein the command includes a C-move command;
   sending, by the client computing device, a remote polling request to the remote computing device;
   sending to the client computing device, by the remote computing device and in response to the remote polling request, the command to move the medical data; and
   executing, by the client computing device, the command to move the medical data, wherein executing the command to move the medical data includes sending the medical data to the remote computing device.

2. The method of claim 1, further including:
   storing new content data having a DICOM format at remote data storage memory of the remote computing device; and
   sending to the client computing device, by the remote computing device and in response to the remote polling request, the new content data.

3. The method of claim 2, further including:
   encrypting the new content data by the remote computing device; and
   decrypting the new content data by the client computing device.

4. The method of claim 1, further including:
   receiving, by the client computing device, command inputs including a command to store or move medical data from another healthcare entity;
   storing, by the client computing device and in a client-side unique queue, the command to store or move medical data from the another healthcare entity;
   sending, by the remote computing device, a client polling request to the client computing device; and
   sending to the remote computing device, by the client computing device and in response to the client polling request, the command to store or move medical data from the another healthcare entity.

5. The method of claim 4, further including:
   sending a patient document to the client computing device, by the remote computing device and in response to the command to store or move medical data from the another healthcare entity.

6. The method of claim 5, further including:
   encrypting the patient document by the remote computing device; and
   decrypting the patient document by the client computing device.

7. The method of claim 1, further including:
   receiving, by the client computing device, command inputs including a command to store or move local medical data from the PACS system and to another healthcare entity;
   storing, by the client computing device and in a client-side unique queue, the command to store or move the local medical data to the another healthcare entity;
   sending, by the remote computing device, a client polling request to the client computing device; and
   sending to the remote computing device, by the client computing device and in response to the client polling request, the local medical data.

8. The method of claim 7, further including authenticating, by a client-side secure gateway of the client computing device, the command to store or move the local medical data to the another healthcare entity.

9. The method of claim 7, further including:
   encrypting the local medical data by the remote computing device; and
   decrypting the local medical data by the client computing device.

10. The method of claim 1, wherein the medical data includes an image generated by a scanning modality.

11. The method of claim 1, wherein the set of instructions installs a data object on the client computing device which is configured to facilitate communications between the client computing device and the remote computing device.

12. A method for securely sharing patient medical data with a client, the method comprising:
    receiving, at a client computing device, a set of instructions;

instantiating, using the set of instructions, a client-side gateway configured to provide secure connection between the client computing device and a remote computing device;

generating, by the remote computing device, a unique identification value for the client computing device based on at least one property of the client computing device;

storing, by a picture archiving and communication system (PACS) system, local medical data having a DICOM format at a local data storage memory of the client computing device;

receiving, by the client computing device, command inputs including a command to store or move medical data from another healthcare entity;

storing, by the client computing device and in a client-side unique queue, the command to store or move medical data from the another healthcare entity;

sending, by the remote computing device, a client polling request to the client computing device; and sending to the remote computing device, by the client computing device and in response to the client polling request, the command to store or move medical data from the another healthcare entity.

13. The method of claim 12, further including sending a patient document to the client computing device, by the remote computing device and in response to the command to store or move medical data from the another healthcare entity.

14. The method of claim 13, further including:
encrypting the patient document by the remote computing device; and
decrypting the patient document by the client computing device.

15. The method of claim 13, wherein the patient document includes an image generated by a scanning modality.

16. The method of claim 12, wherein the set of instructions installs a data object on the client computing device which is configured to facilitate communications between the client computing device and the remote computing device.

17. A method for securely sharing patient medical data with a client, the method comprising:
receiving, at a client computing device, a set of instructions;

instantiating, using the set of instructions, a client-side gateway configured to provide secure connection between the client computing device and a remote computing device;

generating, by the remote computing device, a unique identification value for the client computing device based on at least one property of the client computing device;

storing, by a picture archiving and communication system (PACS) system, local medical data having a DICOM format at a local data storage memory of the client computing device;

receiving, by the client computing device, command inputs including a command to store or move local medical data from the PACS system and to another healthcare entity;

storing, by the client computing device and in a client-side unique queue, the command to store or move the local medical data to the another healthcare entity;

sending, by the remote computing device, a client polling request to the client computing device; and sending to the remote computing device, by the client computing device and in response to the client polling request, the local medical data.

18. The method of claim 17, further including:
encrypting the local medical data by the remote computing device; and
decrypting the local medical data by the client computing device.

19. The method of claim 17, wherein the local medical data includes an image generated by a scanning modality.

20. The method of claim 17, wherein the set of instructions installs a data object on the client computing device which is configured to facilitate communications between the client computing device and the remote computing device.

* * * * *